(12) United States Patent
Shin

(10) Patent No.: US 6,361,504 B1
(45) Date of Patent: Mar. 26, 2002

(54) BIOPSY NEEDLE, METHOD FOR FABRICATING, AND APPARATUS FOR OPERATING THE SAME

(76) Inventor: Myoung Chul Shin, Samik Beach Town 202-1202, 148, Namcheon 2 dong, Suyoung-ku, Pusan (KR), 613-012

( * ) Notice: Subject to any disclaimer, the term of this patent is extended or adjusted under 35 U.S.C. 154(b) by 0 days.

(21) Appl. No.: 09/402,280

(22) PCT Filed: Mar. 31, 1998

(86) PCT No.: PCT/KR98/00074
§ 371 Date: Dec. 3, 1999
§ 102(e) Date: Dec. 3, 1999

(87) PCT Pub. No.: WO98/43541
PCT Pub. Date: Oct. 8, 1998

(30) Foreign Application Priority Data

Mar. 31, 1997 (KR) .............................................. 97-11616

(51) Int. Cl.[7] ................................................ A61B 10/00
(52) U.S. Cl. ........................ 600/562; 600/567; 600/568; 606/167; 606/181
(58) Field of Search ................................. 600/562, 564, 600/566, 567, 568; 606/167, 170, 180, 181, 182, 185

(56) References Cited

U.S. PATENT DOCUMENTS

| | | | | |
|---|---|---|---|---|
| 4,403,437 A | * | 9/1983 | Shuman | 43/36 |
| 5,177,759 A | * | 1/1993 | Marable et al. | 372/61 |
| 5,575,780 A | * | 11/1996 | Saito | 604/272 |
| 5,590,655 A | * | 1/1997 | Hussman | 600/426 |
| 5,733,266 A | * | 3/1998 | Gravlee, Jr. | 604/272 |
| 5,788,679 A | * | 8/1998 | Gravlee, Jr. | 604/272 |
| 5,810,834 A | * | 9/1998 | Heyman | 606/107 |
| 5,830,219 A | * | 11/1998 | Bird et al. | 606/130 |
| 5,871,495 A | * | 2/1999 | Mueller | 606/185 |
| 5,971,939 A | * | 10/1999 | DeSantis et al. | 600/562 |
| 5,976,164 A | * | 11/1999 | Bencini et al. | 606/170 |
| 5,980,469 A | * | 11/1999 | Burbank et al. | 600/567 |

* cited by examiner

Primary Examiner—Eric F. Winakur
Assistant Examiner—Charles Marmor, II
(74) Attorney, Agent, or Firm—Paul & Paul

(57) ABSTRACT

The present invention provides a hollow tubular shaped biopsy needle having a hollow elliptical cross section shaped lumen therethrough, and the method for fabricating the needle and the apparatus for operating the needle. The structure of the biopsy needle of this invention is simple and easy to fabricate, and thus the production cost can be reduced. In comparison of the smaller diameter of this invented biopsy needle to the diameter of the other biopsy needles, the size of the extracted sample will be bigger and wounds of the patient can be less. The apparatus of this invention will help to reduce the operating force during extracting tissue samples, and helps rotation and straight movements of the needle.

10 Claims, 12 Drawing Sheets

US 6,361,504 B1

BIOPSY NEEDLE, METHOD FOR FABRICATING, AND APPARATUS FOR OPERATING THE SAME

FIELD OF THE INVENTION

This invention relates to a biopsy needle for extracting tissue samples, the method for fabricating the same, and the apparatus for operating the needle.

BACKGROUND OF THE INVENTION

The most widely used biopsy needles are a Silverman Needle and a Core Needle, which are generally called names in the field, The Silverman needle, as shown in FIG. 1, has an outer cannula 1 whose vertical hollow cross section is a circle, and a split needle 3 whose distal end is split to extract tissue samples. When using the needle of FIG. 1, the outer cannula 1 is forcibly inserted to an aimed internal organ or a tumor, and then the split needle 3 moves forward out of the cannula 1 into the organ. At that time, the split distal ends of the needle 3 become wide open due to elasticity of the needle and resistance of the tissue of the organ. When the cannula 1 reaches to an aimed organ, the needle 3 retracts and grips the tissue, as shown in FIG. 2. In this state, rotating the outer cannula 1 and the split needle 3 about its longitudinal axis once or twice separates the gripped sample from the tissue.

FIG. 3 shows a Core Needle having an outer needle 5 whose vertical hollow cross section is circle-shaped, and an inner needle 7 for gripping the tissue inside the outer needle 5. The inner needle 7 is a solid tubular body not to admit unnecessary tissue to enter the outer needle, and has a groove 7a about 4 or 5 mm distant from the distal end for acquiring sample.

When using the Core needle, the outer needle 5 advances into the aimed internal organ with the inner needle 7, which firstly moves forward into the tissue and the groove 7a of which accommodates samples of the aimed tissue, after that the outer needle 5 moves more into the tissue to remove the samples contained in the groove 7a from the tissue.

In case of the Silverman needle explained above, to extract enough samples, the outer cannula should be of a larger diameter, since the samples are acquired by the split needle inside the outer cannula. Also, it has been used only in soft organs, since the hardness of the split needle is not strong enough to penetrate into a hard tissue.

In case of Core needle, it can not extract enough samples either, since the samples are acquired by a groove of the inner needle. Thus, to get the enough samples, most users uses a big diameter Core needle or extracts samples several times. Also, since the groove is located about 4 to 5 mm away from the dismal end, it is difficult to acquire an aimed positioned sample and the inner needle should move forward more deeply than the position of the aimed tissue, which may hurt adjacent organs without intention.

Also, this kind of needle can not be mounted on an auto biopsy gun, since the gun generally shoots needles only to a fixed determined depth. Thus, the needle should be handled by hand, which needs more than 20 kgf in some cases.

That is to say, since the needles of the types explained above uses an outer needle for penetrating and an inner needle for acquiring samples, the size of acquired samples are small comparing thickness of the outer needle, thus the size of the outer needle needs to be larger for enough samples, or the operation should be done several times, both of which may wound organs in many points.

Also, both the needles cannot acquire liquid or gaseous phased samples. And since both Silverman and Core needles can be used in a somewhat deep organs, it is inconvenient to extract samples from cuticle or pathological tissues.

Other biopsy needles are disclosed in U.S. Pat. Nos. 5,251,641, 4,926,877, and 5,526,821, which are not being used in the field. The 877' patent has the same problem as the above two needles in that the whole cross section area of the outer needle is not contributed to acquire samples.

It is therefore an overall object of present invention to provide a biopsy needle with a small size (diameter) which can enlarge the size of the acquired samples by the needle.

It is an another object of the invention to provide a method for fabricating the above needle.

It is still another object of the invention to provide an apparatus for operating the biopsy needle.

Other objects and advantages will be more fully apparent from the following disclosure and appended claims.

SUMMARY OF THE INVENTION

The invention discloses a needle which can be used to acquire samples without an inner needle, thus it can acquire relatively bigger sample than the needle assembly having an inner needle and an outer needle.

The needle of this invention is hollow tubular shaped, and the cross section of the hollow section taken vertically to the longitudinal direction is elliptical shaped.

The samples captured in the needle are extracted by twisting the needle, which is possible since the hollow section of the needle is not circle-shaped.

Separating the samples from the aimed tissue may be accomplished by a needle with a twisting rectangular or triangular or any polygonal shaped hollow section, but, it is preferable to make the hollow section of the needle elliptical regarding convenience of manufacturing, impact of twisting tissue, size of samples acquired.

Furthermore, the needle of the invention has an inwardly beveled distal end to acquire bigger size of the samples.

Though the needle is basically structured to have an elliptical hollow section and an inwardly beveled distal end, to improve the separation of samples a portion of the distal end of the needle is outwardly beveled, whereas the other portion is inwardly beveled.

Meanwhile, the method for manufacturing the biopsy needle of the invention has providing a hollow tube, drawing the hollow tube so that the hollow section of the tube becomes elliptical shaped, cutting the tube in a predetermined length, and machining an distal end of the tube to be inwardly beveled.

To improve penetrating, the method may further comprise machining the outer circumferential portion of the distal end of the tube to be outwardly beveled after machining the distal end to be inwardly beveled.

Alternatively, another method of the invention has a step of machining the distal end of the tube so that a portion of the distal end is outwardly beveled and that the other portion is inwardly beveled.

According to the invention, to make the inner hollow section of the needle elliptical, pressing the tube to make whole tube elliptical may be adapted instead of drawing the tube. This method is useful, when the diameter of the tube is so small that drawing the tube to have a hollow elliptical cross section is difficult.

This invention also discloses the apparatus for handling the biopsy needle, which has an acting part where the needle is mounted and the needle is translated and rotated, and a driving part for transmitting translation force and rotation force to the acting part. The apparatus further comprises a handling part for easy handling of the driving part. When the structure of the aimed tissue is hard and requires a big force, the acting part may be divided as a translation acting part and a rotating acting part.

DETAILED DESCRIPTION OF THE INVENTION

Now the embodiments of the invention will be explained in detail with reference to the attached drawings, where the distal ends of the needles are mainly shown, but the other end of the needle, or proximal end where user's hand or any apparatus for operating the needle acts is omitted for simplicity.

(1st Embodiment)

Figure 1:
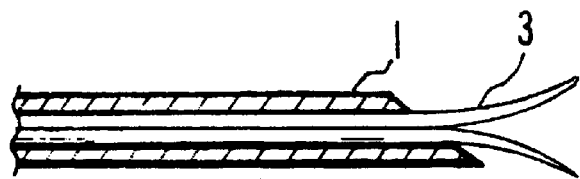
FIG. 1 is a partial horizontal cross section of a Silverman Needle.
Figure 2:
FIG. 2 is a view similar to FIG. 1 showing the operating condition of the needle of FIG. 1.
Figure 3:
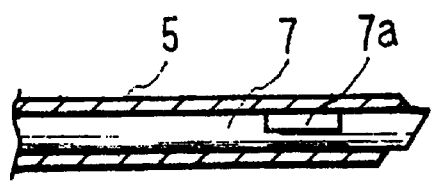
FIG. 3 is a partial horizontal cross section of a Core Needle.
Figure 4:
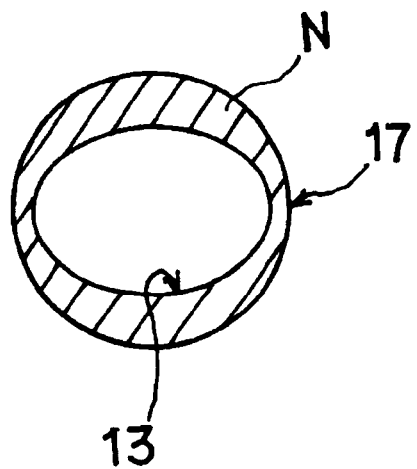
FIG. 4 is a vertical cross section of a needle according to the first embodiment of the invention.

The biopsy needle of this embodiment has an elliptical hollow cross section when viewed in its longitudinal direction, as shown in FIG. 4.

The outer surface 17 of the needle N is circular shaped, and the inner surface 13 which defines lumen is elliptical shaped.

Elliptical or race-track shape of this invention means not a mathematically defined ellipse which requires a certain formula, but a commonly or generally meant ellipse which only requires a long diameter and a short diameter comparing a circle having only diameter.

The ratio of the long diameter and the short diameter is not so larger than 1, since the cross section area of the needle N for extracting the samples becomes smaller and the rotating resistance rises, as the ratio becomes larger. Thus it is preferable that the ratio between the long diameter and the short diameter of the hollow cross section is between 1.6:1 and 2.0:1 regarding rotating resistance and size of the extracted sample.

While the biopsy needle N of this invention is moving to an aimed position of tissue, a portion of the tissue is cut and enters the elliptical hollow section tightly. At the same time, as the needle N is rotated once or twice, the sample in the hollow section is separated from the original tissue due to the shape of the hollow section. The sample in the lumen is finally extracted by pulling back the needle.

U.S. Pat. No. 4,926,877 also discloses a race-track shaped hollow tubular needle, but the needle has an additional separating means for separating samples from the tissue, which is not necessary in this invention. Also all the samples captured in the racetrack shaped hollow section are not extracted because of the separating means.

Figure 5:
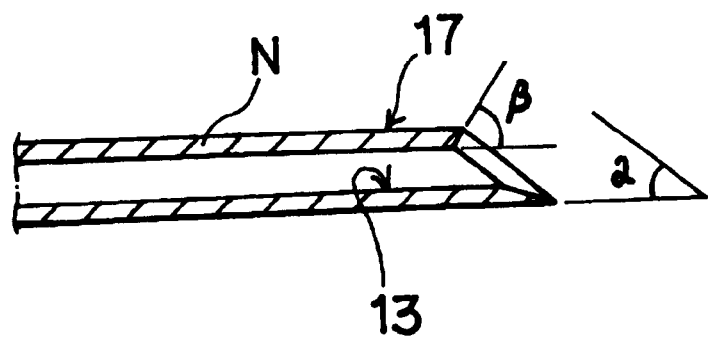
FIG. 5 is a partial horizontal cross section of a needle according to the first embodiment of the invention.

The distal end 19 of the needle N is preferably tapered by an acute angle $\alpha$ relative to the needle's longitudinal axis to improve the ease with which the biopsy needle may be inserted into the patient, as shown in FIG. 5. The tapered edge 19 of the needle is cut inwardly to increase the size of the tissue entered in the lumen during proceeding the needle to the aimed tissue. The angle between the longitudinal axis of outer surface 17 of the needle N and cut beveled surface is acute angle $\beta$.

Figure 6:
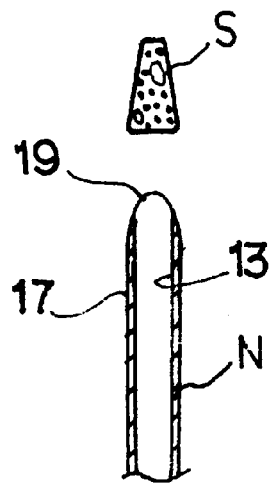
FIG. 6 is a partial horizontal cross section of a needle with an outwardly beveled leading edge and a sample acquired by this needle.
Figure 7:
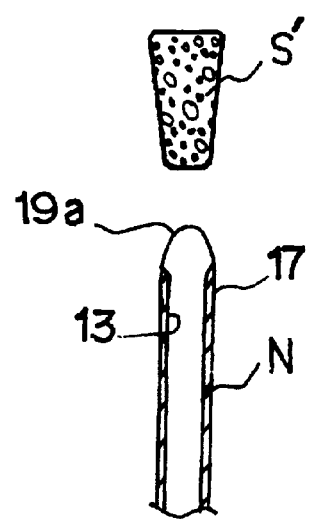
FIG. 7 is a view similar to FIG. 6 showing a needle with an inwardly beveled leading edge and a sample acquired by this needle.

Referring to FIGS. 6 and 7, according to an experiment with two needles having same diameter as each other the sample S' extracted by the biopsy needle having an outwardly beveled leading edge 19a looks a cone. The base portion of which is an outer portion of the sample, which means that as the needle with an outwardly beveled edge 19a is inserted to the patient, the tissue is cut by an inner surface of the needle, thus the size of the captured sample becomes smaller and finally the sample becomes cut.

The sample S extracted by the biopsy needle N of this embodiment which has an inwardly beveled leading edge 19 also looks a bigger cone than the biopsy needle with outwardly beveled leading edge 19a, but the base portion of which is an inner portion of the tissue sample, which means that as the needle is inserted to the patient, the tissue is cut by an outer surface 17 of the needle, thus the size of the captured sample becomes larger.

The beveled angle $\beta$ can be determined properly considering thickness and outer diameter of the needle.

According to this embodiment, since the needle N has an elliptical hollow lumen, the sample can easily be separated from the tissue and does not need any other means for separating samples such as inner cannula, which means that the size of the sample by the needle of this invention is bigger than any needle of prior art.

Also since the sample can be captured in the direction of longitudinal axis of the needle, the operation for extracting sample can be more accurately done. That is, when the aimed tissue is near the tissue not to be touched for patient's safety, operator can easily escape from the danger.

Since the size of the sample to be extracted depends on the depth of the inserted needle, the amount can be determined properly by the operator. And when the needle is mounted to an injector, the liquid phased or gaseous samples can be easily obtained, whereas they can not be obtained by a Silverman needle or a Core needle, since neither of them can be removed of the inner needle only.

Though this embodiment discloses a needle of elliptical cross section and inwardly beveled leading edge, the needle having inwardly beveled leading edge only or the needle only having a hollow elliptical cross sectioned lumen can be a useful biopsy needle.

(2nd embodiment)

Figure 8:
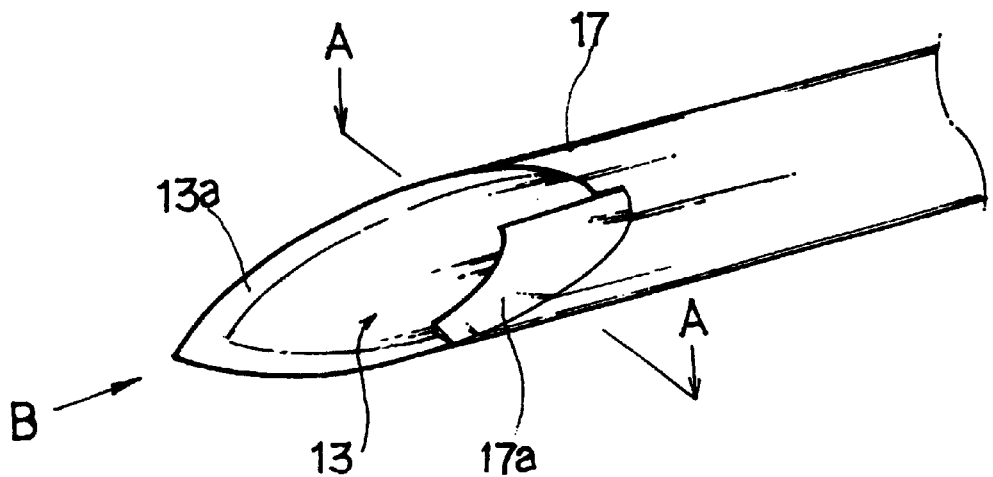
FIG. 8 is a partial perspective view showing a needle according to the second embodiment of the invention.
Figure 9:
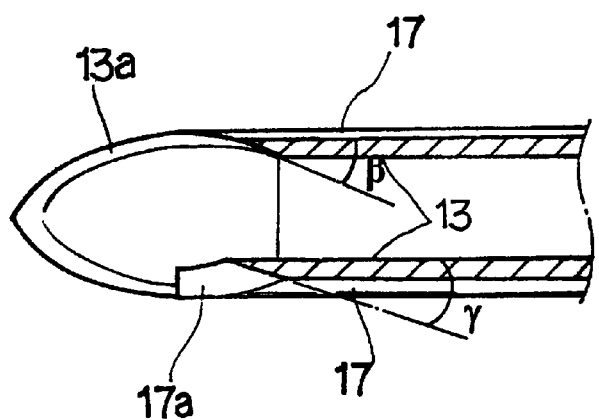
FIG. 9 is a partial cross section taken A—A line of FIG. 8.
Figure 10:
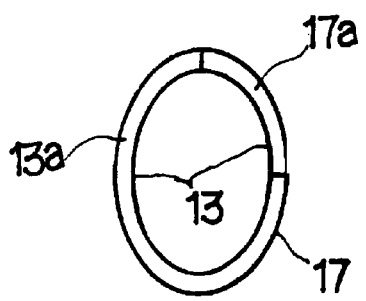
FIG. 10 is a view viewed in B direction of the FIG. 8.

The needle of this embodiment is similar to that of the first embodiment since most portion of the tapered leading edge 19 of the needle is beveled inwardly and can extract large size of sample, but about quarter portion of the leading edge is outwardly beveled, as shown in FIG. 8. FIG. 9 explicitly shows that the outwardly beveled portion 17a make an acute angle with the longitudinal axis of the inner surface of the needle.

Partially outwardly beveled leading edge 17a of the needle aims to improve the ease with which the sample captured in the lumen can be separated from the tissue. The sample captured by the needle of this embodiment is cut to be separated from the tissue since the inwardly beveled portion 13a and the outwardly beveled portion act as a pair scissors while the sample captured by the needle of the first embodiment is torn to be separated from the tissue.

The position of the outwardly beveled portion 17a shown in FIG. 9 is for example, and its portion is about quarter of the leading edge. If more portion for example, half portion of the leading edge is outwardly beveled, the size of the sample will be smaller due to the outwardly beveled leading edge.

Though to adopt this embodiment the cross section of the needle can be elliptical or circular, it is preferable that the cross section of the needle is elliptical shaped.

(3rd embodiment)

This embodiment aims to provide a needle with a stylet for acquiring sample positioned deep under the skin.

As explained regarding the first embodiment, the needle with inwardly beveled edge can extract much bigger sized sample than the Silverman needle or Core needle both of which has an inner and an outer cannula especially when the aimed samples are the outer skins.

Figure 11:
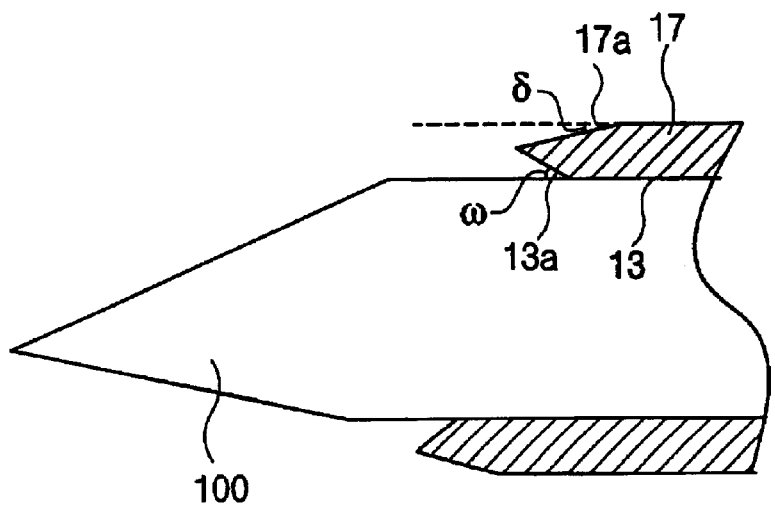
FIGS. 11 and 12 are partial horizontal cross sections of a needle according to the third embodiment of the invention, each of which has a different stylet from each other.
Figure 12:
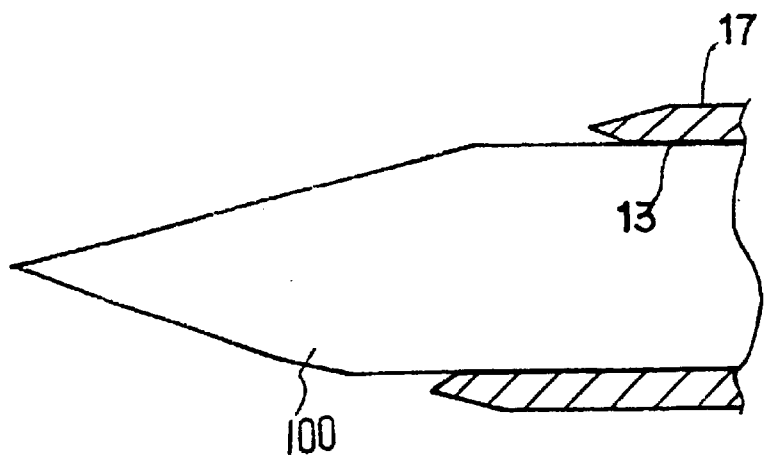

By the way, when the aimed position of the needle is deep under the skin, a stylet 100 is necessary for preventing unnecessary tumor such as outer skin from entering the needle and for releasing resistance of outer tumor. The stylets 100 shown in FIGS. 11 and 12 are just examples.

Since the needle of the invention is inserted to the aimed position with the stylet therein but the sample is acquired only by the needle without stylet 100, the size of the sample acquired by this embodiment is larger than by the Silverman or Core needle.

While the needle with the stylet 100 advances into the internal organs, the inwardly beveled portion 13a of the needle of above embodiments will experience resistance, which may result in damage of the surrounded organs.

This embodiment aims to improve this problem, and discloses a needle with inwardly beveled in the inner circumferential portion of the leading edge and the outwardly beveled portion 17a of the outer circumferential portion of the leading edge. The outwardly beveled portion 17a of the leading edge is for reducing resistance of the organs, and the inwardly beveled portion 13a of the leading edge is for increasing size of the samples acquired.

The angle of outwardly bevel is similar to the beveled angle of the stylet 100 to make easy inserting and the angle of the inward bevel is preferably gentle, as shown in FIGS. 11 and 12. That is, the outwardly beveled angle γ is slightly smaller than the inwardly beveled angle ω.

The shape of stylet is not limited to what FIGS. 11 and 12 show, but may be variable.

(4th embodiment)

U.S. Pat. No. 5,526,821 discloses a needle which increases in diameter from a distal end to a proximal end to aid in acquiring a tissue sample and retaining it within the lumen of the needle, which can be incorporated to the above embodiments.

Figure 13:
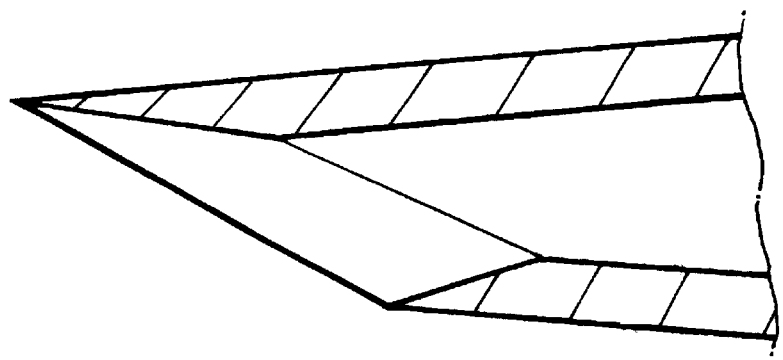
FIG. 13 is an enlarged partial horizontal view of the needle according to 4th embodiment of the invention.
Figure 14:
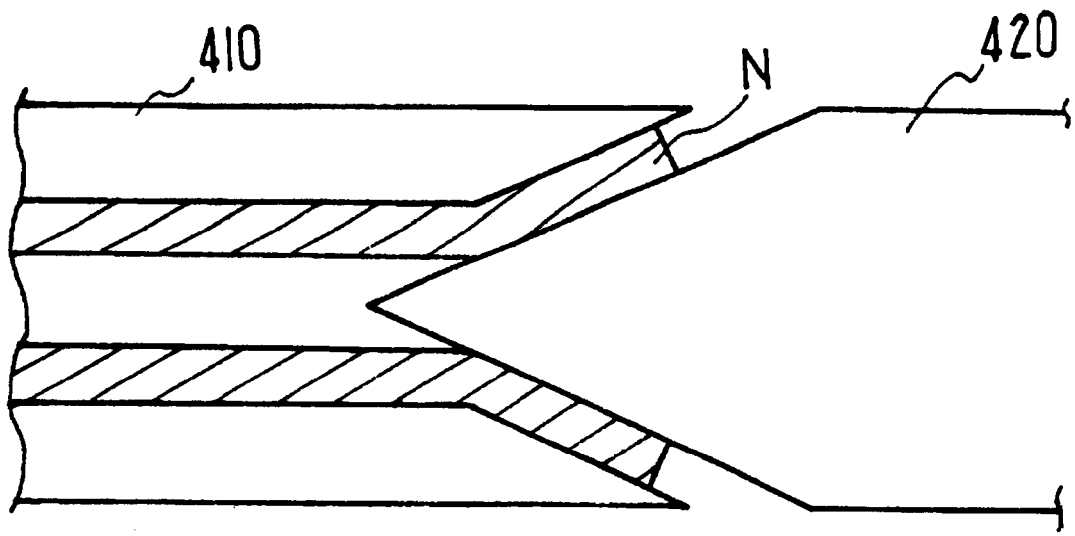
FIG. 14 is a partial view in order to show the method for making the needle, according to the 5th embodiment of the invention.

FIG. 13 is an enlarged partially shown cross sectional view of the needle according to this embodiment, which increases in diameter from a distal end to proximal end and has inwardly beveled leading edge 19.

This shape of the needle helps inserting the needle into the patient and the sample by the needle N can be retained in the lumen of the needle during the withdrawing of the needle.

(5th embodiment)

The needle of the inwardly beveled leading edge can be manufactured by the method explained below.

First, a hollow tube of steel is provided, and the hollow tube is drawn so that the hollow portion of lumen of the tube becomes to have an elliptical shaped vertical cross section, but the cross section of the outer surface of the tube is preferably circle shaped.

After than one end of the tube is cut in a predetermined length in acute angle α, as shown in FIG. 5. After that, the cut tube N is inserted into a frame 410 which is a hollow member having inner diameter similar to the outer diameter of the tube N and having inwardly beveled leading edge, which can be easily machined since the diameter of the frame 410 is much larger than that of the of the biopsy needle.

Next, to enlarge diameter of the leading edge, a solid member 420 which has a conical shaped leading portion is pressed to insert into the tube. The conical angle of the solid member 420 is same as beveled angle of the frame 410. The leading edge of the tube N becomes enlarged with the same angle of the slope of the frame 410 and the solid member 420 though this process and is withdrawn from the frame 410.

Figure 15:
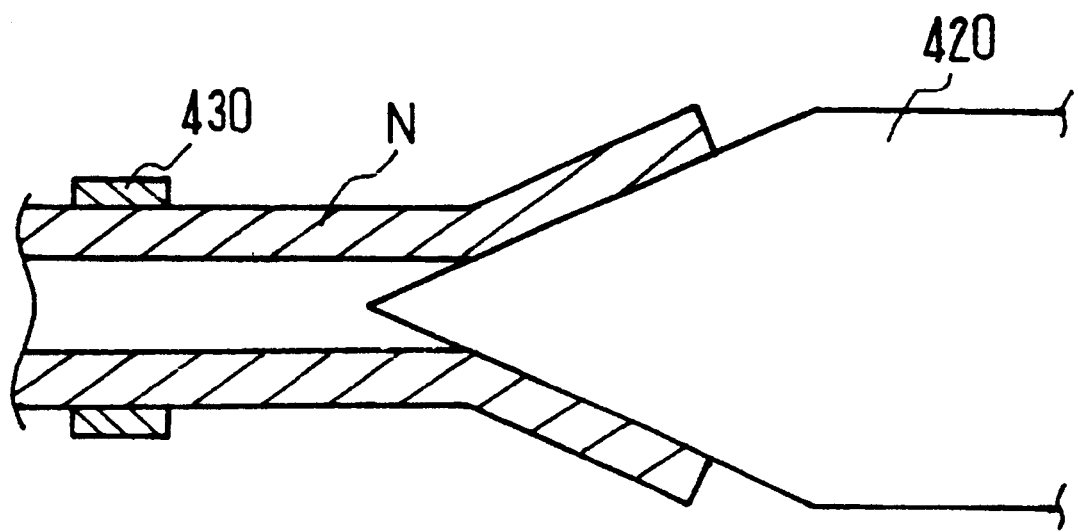
FIG. 15 is a view similar to FIG. 14 showing a cutter 430 to cut the protruded or enlarged portion of the needle N.

And the enlarged leading edge of the tube N is cut by the cutter 430 having inner diameter same as the inner diameter of the frame 410 or outer diameter of the unchanged portion of the tube N, as shown in FIG. 15.

The needle manufactured by the above method has a lumen which has elliptical cross section as shown in FIGS. 4 and 5 and has an inwardly beveled leading edge.

To make the cross section of the lumen of the needle elliptical, the drawing is adopted so that the cross section of the outer surface of the needle maintain circular shape. In case of small sized needle, since it is difficult to draw a tube to have an elliptical hollow section, the tube may be pressed with a predetermined force in the perpendicular direction of the longitudinal axis of the tube, which may cause entire tube including outer surface is shaped elliptically. Pressing tube cannot be applied to a relatively big tube, for example over 2 mm diameter, since the elliptical cross section of the needle increases rotating resistance, which may hurt organs.

(6th embodiment)

The apparatus or assembly for handling the biopsy needle of the invention is means for inserting and rotating the needle having a lumen with elliptically shaped cross section, and has an acting part where the needle is mounted and the needle is inserted and rotated, and a driving part for transmitting translation force and rotation force to the acting part. The apparatus further comprises a manipulating part for easy handling of the driving part.

Figure 16:
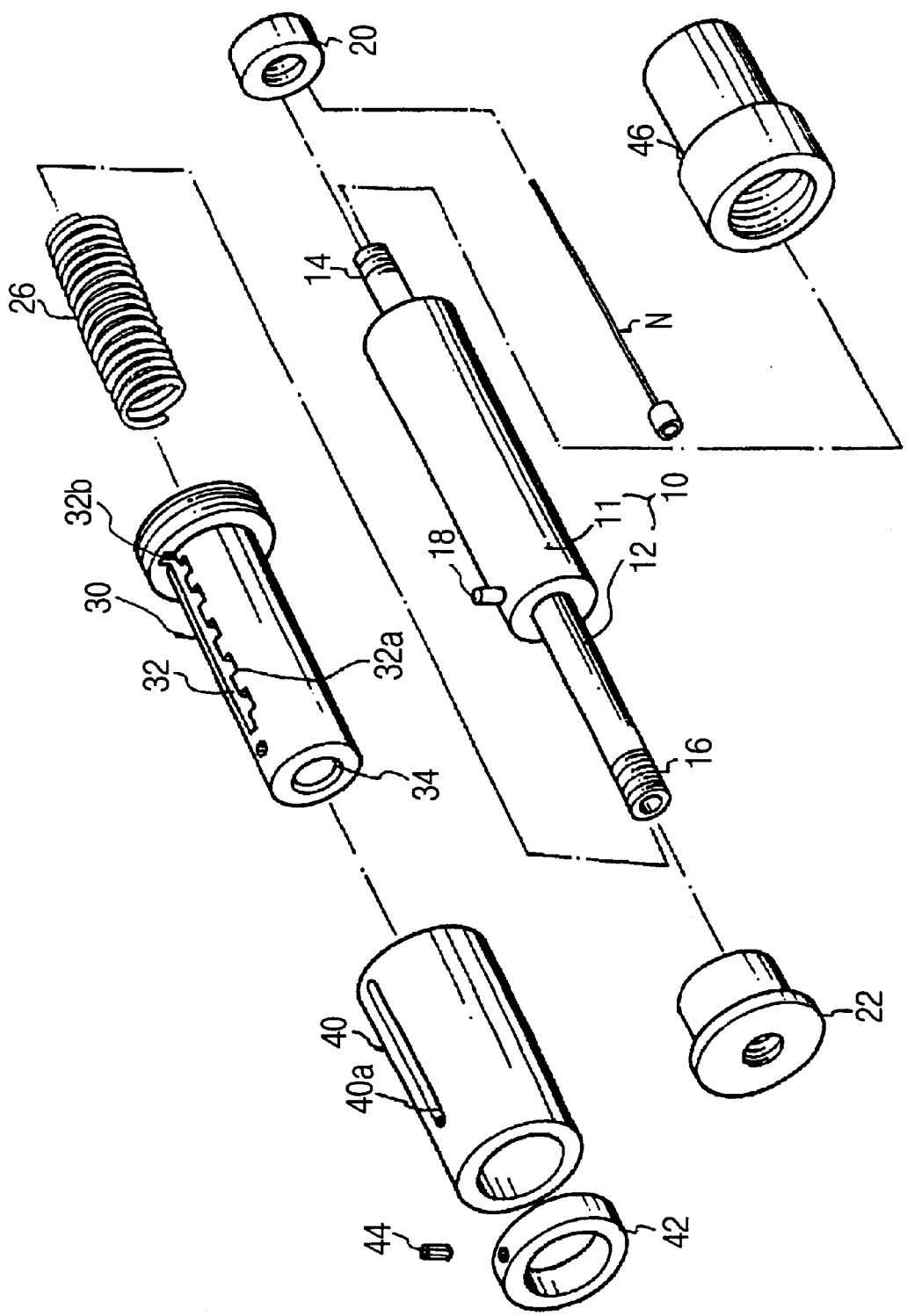
FIG. 16 is a perspective view of an apparatus according to 6th embodiment of the invention, showing all the components are disassembled.

The apparatus shown in FIG. 16 is characterized in that the acting part has a spring.

An end of the piston or hollow pipe 10 having a long-diameter portion 11 and a short-diameter portion 12 has a screw 14 to engage cap 20 for mounting and fixing or removing the biopsy needle N, the other end of the piston 10 has another screw 16 to engage handle 22, and in one side of the outer circumference of the long-diameter portion 11, a stopper 18 is formed protruded.

The short diameter portion 12 of the piston 10 is inserted into the inner case 30 with a spring 26.

The inner case 30 has a guide slot 32 through which the stopper 18 of the piston 10 can pass, and which has a plurality of fixing recesses 32a formed in regular intervals for stopping the stopper 18 temporally in a predetermined position.

The inner case 30 has a supporting wall 34 which has a hole with similar diameter to the outer diameter of the short diameter portion 12 of the piston 10, and which fixes one end of the inserted spring 26 and prevents it from shaking. The other end of the spring 26 is secured by the piston 10, thus the spring 26 provides both compressive elasticity along the longitudinal axis of the piston 10 and twisting elasticity in the rotating direction around the longitudinal axis of the piston 10.

The inner case 30 is inserted loosely into the outer case 40 so that it can rotates freely without any external action, and is prevented from being disassembled by a ring-shaped release 42 and a locking pin 44.

The slot 40a formed in the longitudinal direction of the outer case 40 is for the stopper 18 to move, and through the slot 40a the position of the stopper 18 can be confirmed.

Unexplained member 46 is a guide member screwed to the proximal end of the inner case 30, which guides the piston 10.

The operation of the apparatus having a structure explained above will be explained with reference to FIG. 17.

For operation, at first the needle N having elliptical cross sectioned lumen should be engaged to the leading end of the piston 10 and fixed by the cap 20.

Next, the piston 10 should be rotated once or twice while the stopper 18 does not inserted into the slot 32, and be withdrawn to compress the spring 26 until one of the recesses 32a is chosen for the stopper 18 to be temporally fixed while the stopper 18 is introduced through the guide slot 32. In this state the spring 26 has twisting load and compressive load.

Finally, while the leading edge of the needle N is being aimed to a patient, releasing the stopper 18 from the recess 32a by rotating the release 42 causes the compressed spring 26 to expand. While the stopper 18 is moving along the guide slot 32, the spring 26 cannot rotate, but just expands to reach an aimed position of tumor. After passing the end 32b of the slot 32, the stopper 18 can rotate with the piston 10 once or twice. The sample is acquired by the rotating of the needle N with an elliptical cross sectional lumen.

(7th embodiment)

Figure 17:
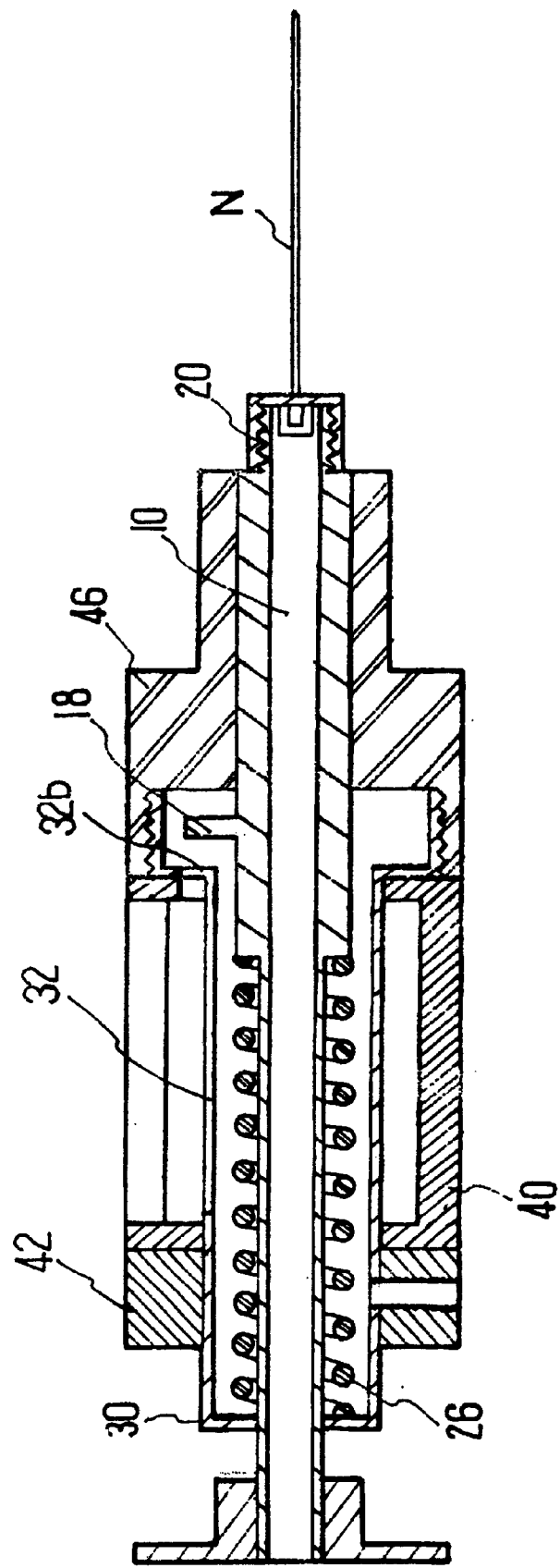
FIG. 17 is a horizontal cross section of the apparatus of FIG. 16.

Generally it requires more than 20 kgf force to insert a biopsy needle into a patient, which can be done by enlarging spring constant of the spring 26 of FIGS. 16 and 17. However, since to manipulate a spring with a big spring constant requires also big compressing force in proportion, to relieve the handling force is required.

Figure 18:
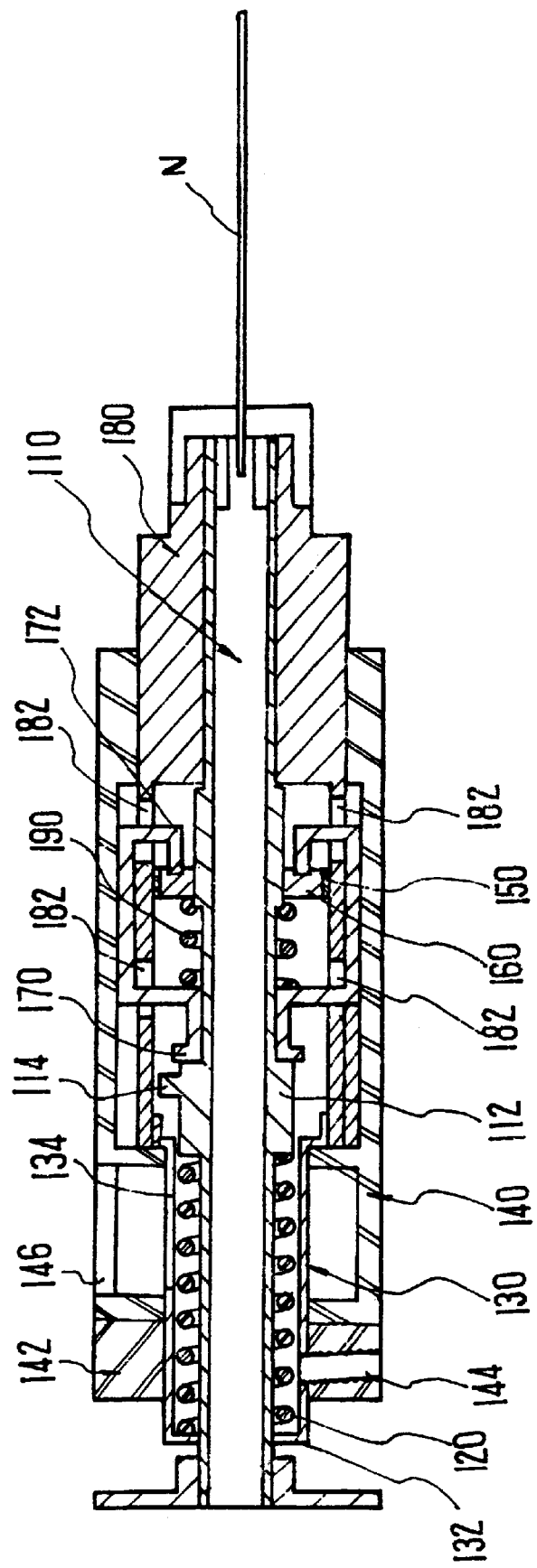
FIG. 18 is a horizontal cross section of the apparatus according to the 7th embodiment of the invention.

The apparatus of this embodiment, which is shown in FIG. 18, is an application of the sixth embodiment of the invention, but has two separated elastic means, one for moving the acting part straightly, the other for rotating it, in order to minimize handling force.

A compression spring 120 for translating the piston 110 is mounted on the inner case 130 near the proximal end of the piston 110, is compressed as the piston 110 withdraws, and is supported by a supporting portion 112 of the piston 110 and the proximal end wall 132 of the inner case 130.

In the inner case 130 is formed a guide slot 134 so that the stopper 114 protruded from the piston 110 can pass, and a plurality of recesses for temporally fixing the stopper 114 in a predetermined position, which is similar to those of the previous embodiment, though they are not shown in FIG. 18.

The inner case 130 is inserted loosely into the outer case 140 so that it can rotates freely without any external action, and is prevented from being disassembled by a ring-shaped release 142 and a locking pin 144 penetrating the inner case 130.

To confirm the action of the stopper 114, a slot 146 is formed in the outer case 140.

Figure 19:
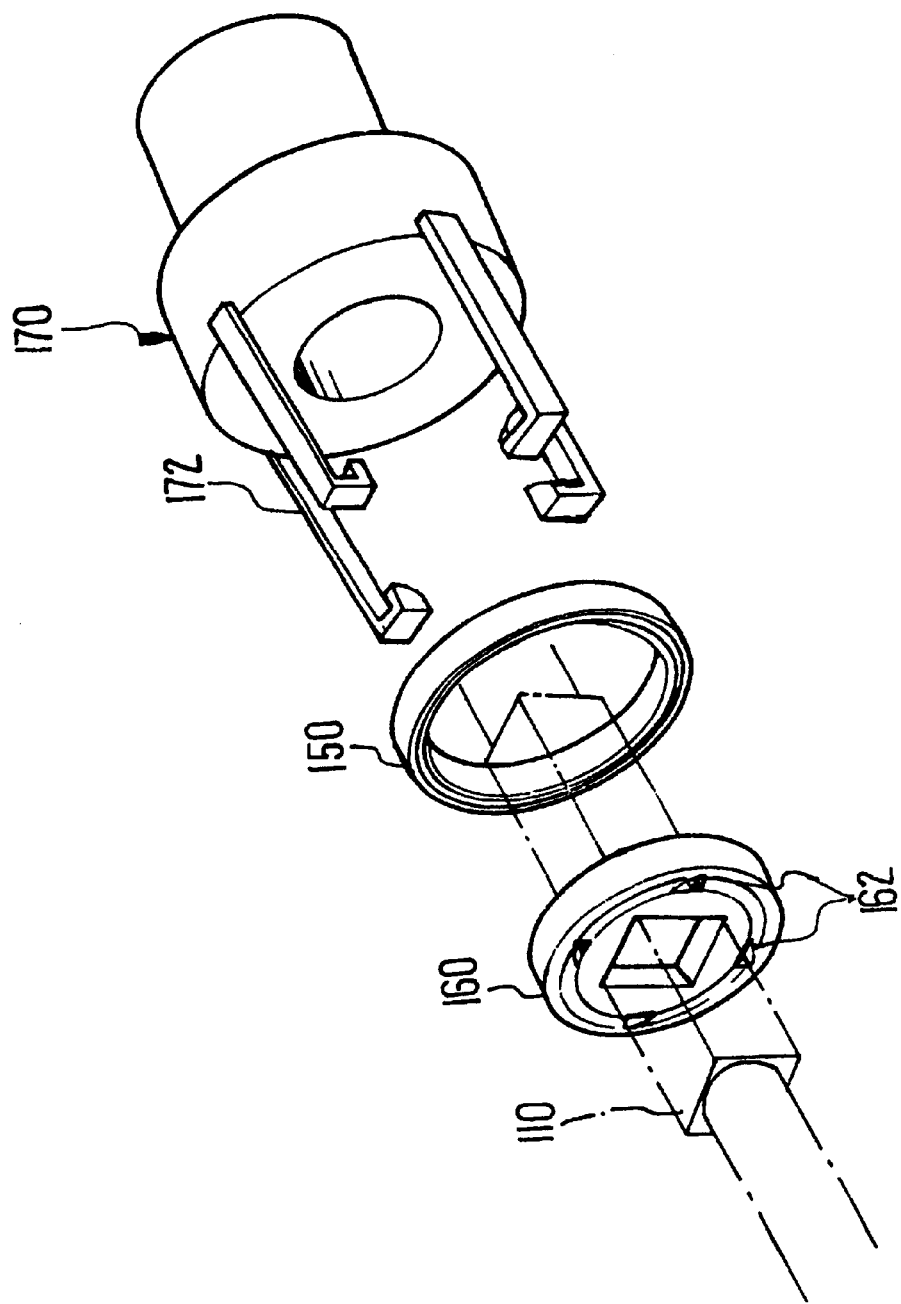
FIG. 19 is an enlarged view of some major components of FIG. 18.

The rotation movement of the piston 110 is accomplished by a spiral spring 150, and a locker 160 and a striker 170 for temporally fixing the compresses spiral spring 150, which is shown in FIG. 19. The locker 160 is a circular plate having a rectangular passage in the central position and 4 one-way holes 162 disposed around the passage.

The striker 170 is a hollow circular plate having four fixing hooks 172 each end of which matches the one way hole 162 of the locker 160.

The locker 160 and striker 170 is splined to the piston 110, and the fixing hooks 172 are inserted into the slot 182 of the guide member 180 to move in a predetermined distance, and the locker 160 is supported by the compression spring 190 inserted in the piston 110 in order for the oneway holes 162 to be engaged with the fixing hooks 172, as shown in FIG. 18.

One end of the spiral spring 150 is fixed to the outer surface of the locker 160, and the other end of the spring 150 is fixed to the guide member 180.

Of the outer surface of the piston 110 there is a rectangular cross sectioned portion for being engaged with the rectangular passage tightly, whereas, the piston 110 is tubular shaped with hollow circular cross section to absorb liquid phased or gaseous tissue samples.

The operation of the apparatus having a structure explained above will be explained with reference to FIG. 18.

Rotating the piston 110 in a predetermined angle rotates the locker 160 splined to the piston 110, which compresses the spiral spring 150. In this state, the fixing hooks 172 matches one-way hole (not shown) temporally by the compression spring 190 supporting the locker 160.

Next, withdrawing the piston 110 lets the compression spring 190 be compressed and the stopper 114 protruded from the supporting portion 112 of the piston 110 pass the guide slot 134.

During the withdrawing of the piston 110, to temporally fix the movement of the piston 110 the stopper 114 must be inserted to one of the fixing recesses (not shown) by rotating the piston 110 slightly in the direction of the recesses.

Finally, while the leading edge of the needle N is being aimed to a patient, releasing the stopper 114 from the recess by rotating the release 142 causes the compressed spring 120 to expand. While the stopper 18 is moving along the guide slot 32, the spring 26 cannot rotate, but just expands to move the needle N into the skin. At this time, the supporting 112 portion of the piston 110 strikes the base of the striker 170 to compress the compression spring 190 and moves the striker 170 in a predetermined distance, which release the fixing hooks 172 from the one-way holes of the locker 160, which permits the piston 110 and the needle fixed thereto to rotate by the restoring force of the spiral spring 150.

That is, this embodiments provides a spiral spring for rotation movement and a compression spring for a straight movement, which means that the handling force can be much reduced, since the elastic force of the previous embodiment is divided.

(8th embodiment)

Figure 20:
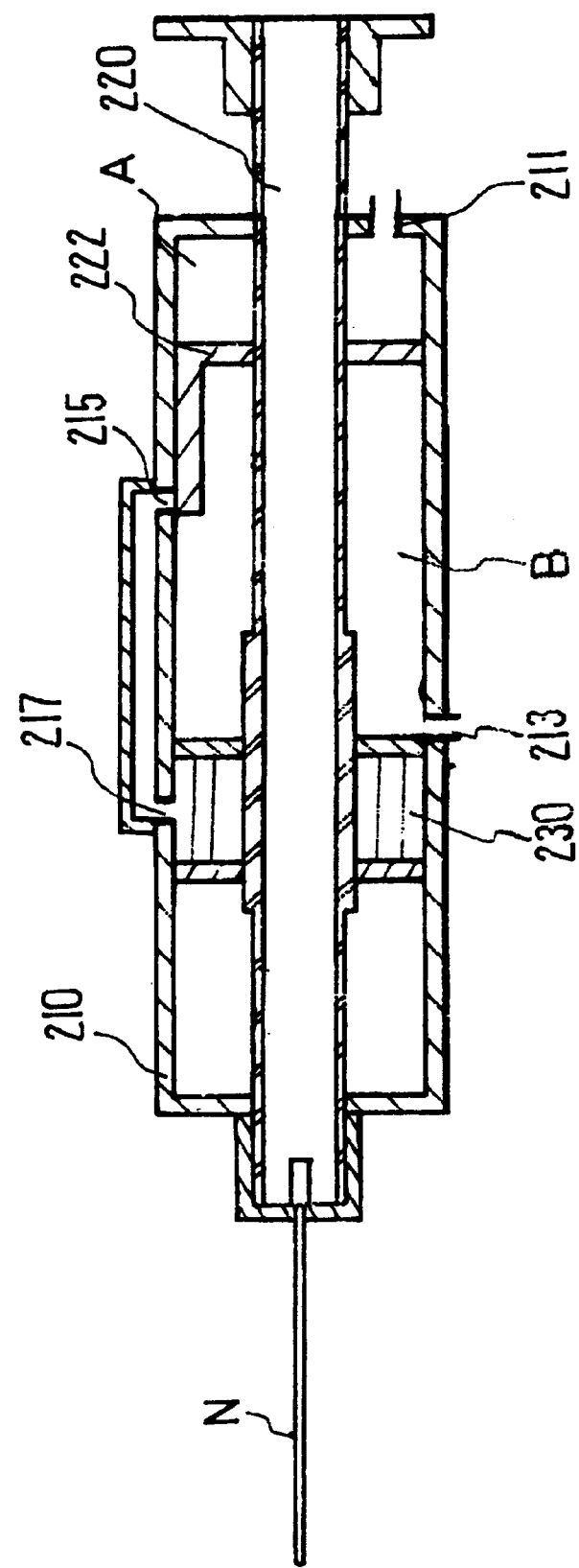
FIG. 20 is a horizontal cross section of the apparatus according to the 8th embodiment of the invention.

The apparatus of this embodiment utilize pneumatic pressure for straight movement and rotation movement of the needle, as shown in FIG. 20.

The cylinder 210 of this embodiment has a spinning wheel shaped blade portion 230 dividing inner portion of the cylinder 210.

The piston 220 in the cylinder 210 of this embodiment has a plate 222 fixed to the circumferential surface of the piston 220, dividing two chambers A and B defined by the surrounding cylinder 210 and the plate 220, each volume of which varies in accordance with the movement of the piston 220.

The cylinder 210 has two ports for absorbing compressed air in a predetermined interval, one port 211 of which is formed in the chamber A, and the other port 213 of which is formed in the chamber B.

On the opposite side (upper sided when viewed in FIG. 20) of the two ports 211 and 213 there is formed a third port 215 for the compressed air entered through either of the ports 211 and 213 to pass and for communicating with a 4th port 217 which is formed in the blade portion 230.

The piston 220 is splined to the inner surface of the blade portion 230, and rotates as the blade 230 rotates.

The operation of the apparatus having a structure explained above will be explained with reference to FIG. 20.

Compressed air applied to the first port 211 of the chamber A expands volume of the chamber A, which causes the needle N to be inserted to the organs.

The expansion of the volume of the chamber A and movement of the piston 220 opens the third port 215, through which the compressed air passes to the fourth port 217 to rotate the blade 230, which rotates the piston 220 to separate the samples from the tissue.

The pneumatic pressure for this apparatus can be adjusted regarding density of the aimed tissue, and can control straight and rotation movement of the piston.

(9th embodiment)

Figure 21:
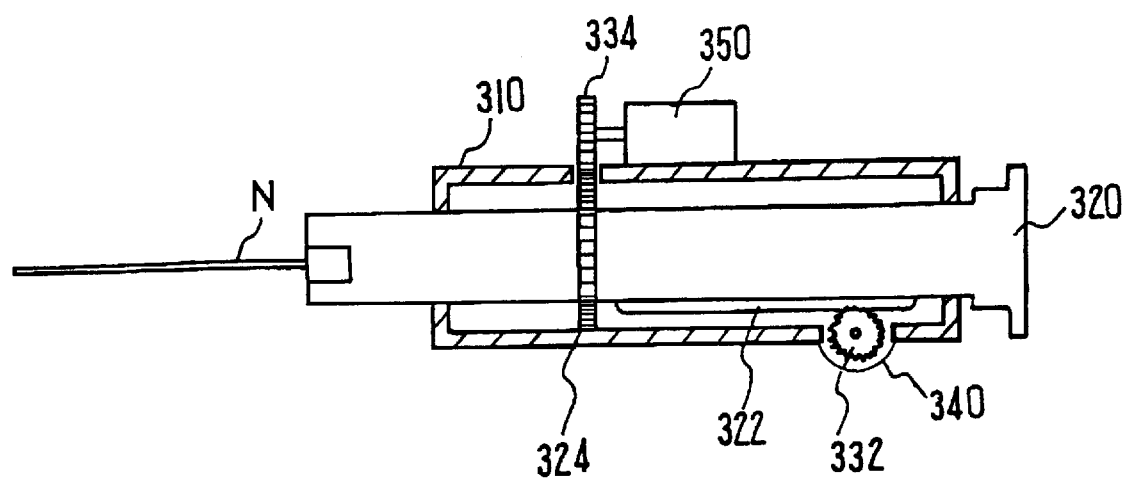
FIG. 21 is a horizontal cross section of the apparatus according to the 9th embodiment of the invention.

The apparatus of this embodiment utilizes a motor for straight and rotation movements of the piston, which is shown in FIG. 21.

A rack 322 is formed on a side surface of the piston 320, and the pinion 332 which meshes the rack 322 is driven by a first motor 340 which is mounted on the cylinder 310.

In the circumferential surface of the piston 310 distant from the rack 322 is mounted a ring gear 324 which meshes a driving gear 334 which is driven by the second motor 350.

The operation of the apparatus having a structure explained above will be explained with reference to FIG. 21.

The first motor 340 drives the pinion 332 to move the piston 320 due to the rack 322 engaged with the pinion 332, to push the needle N to enter the patient.

After that, the second motor 350 drives the driving gear 334 to rotate the meshed ring gear 324 of the piston 320, which makes the needle N rotate and the sample acquired be separated from the tissue.

The motors 340 and 350 for this apparatus can be adjusted regarding density of the aimed tissue, and can control straight and rotation movement of the piston.

According to the above embodiments the needle is fixed to a cap screwed to the piston, but also the needle can be fixed by being forcibly fitted.

Since the structure of the biopsy needle of the invention is simple and easy to manufacture, the production cost may be reduced.

Since the size of the sample can be enlarged with the needle of this invention, the diameter of the biopsy needle can be smaller and wounds of the patient can be less.

Since the sample is extracted through the distal end of the needle, it is easy to control the penetrating depth and to avoid dangerous organs, and it helps to increase the accuracy of the operation.

The liquid-phased or gaseous tissue can be easily acquired by adapting the piston to which fixes the needle, therefore a cystic tumor can be examined and needle-aspiration biopsy can be done by the needle.

Since the needle of the invention is small, and it can be used without anesthesia or under local anesthesia, any harmful disease can be early found.

Still according to the invention, the needle is easy to carry and to sterilize.

It is to be understood that the present invention may be embodied in other specific forms without departing from the spirit or special attributes hereof, and it is therefore desired that present embodiments be considered in all respects as illustrative and therefore not restrictive, reference being made to the appended Claims rather than the foregoing description to indicate the scope of the invention.

I claim:

1. A hollow tubular shaped biopsy needle with a hollow elliptical cross section, comprising:
    a proximal end where manipulating means is applied; and
    a tapered distal end relative to a longitudinal direction, said distal end being inwardly beveled wherein an inner circumferential portion of said distal end is inwardly beveled, and an outer circumferential portion of said distal end is outwardly beveled.

2. The biopsy needle according to claim 1, wherein said needle increases in diameter from said distal end to said proximal end.

3. A method for manufacturing a biopsy needle with an inwardly beveled leading edge, comprising:
    a step of providing a hollow tube;
    a step of drawing the tube so that the tube has a hollow elliptical cross section;
    a step of cutting the tube so that the tube has a predetermined length;
    a step of inserting a solid member having a tapered leading edge into the tube in order to enlarge an elliptically shaped hollow end of the tube; and
    a step of cutting the hollow end of the tube that was enlarged so that the tube has a uniform outer diameter.

4. The method for manufacturing a biopsy needle with an inwardly beveled leading edge according to claim 3, further comprising:
    a step of inserting the tube into a hollow frame having same a similar taper angle before the step of inserting a solid member; and a step of withdrawing the tube from the frame after the step of inserting a solid member.

5. An apparatus for operating a biopsy needle with an elliptical hollow cross section, comprising:

acting means for mounting said needle, moving straight and rotating;

driving means for providing elasticity for the straight movement and the rotational movement; and handling means for controlling said driving means, p2 wherein said acting means comprises a piston having a cap for mounting said needle, and said driving means comprises guiding means surrounding a circumferential surface of said piston for guiding the straight movement and the rotational movement of said piston, and an elastic member located in said guiding means, and said handling means comprises a stopper, a plurality of fixing recesses disposed in a predetermined interval in said guiding means for temporarily fixing said stopper.

6. The apparatus for operating a biopsy needle with an elliptical hollow cross section according to claim 5, wherein said guiding means comprises an inner case and a guiding member screwed to said inner case, said plurality of recesses are formed in said inner case.

7. The apparatus for operating a biopsy needle with an elliptical hollow cross section according to claim 5, wherein said elastic member is a compression spring.

8. The apparatus for operating a biopsy needle with an elliptical hollow cross section according to claim 5, wherein said driving means comprises a first elastic means for driving a straight movement of said piston and a second elastic means for driving a rotational movement of said piston, said first elastic means experiences a translational elastic movement in an inner case near a handling portion of said piston, and said second elastic means is mounted slidably on to a circumferential surface of said piston and experiences a rotational elastic movement.

9. The apparatus for operating a biopsy needle with an elliptical hollow cross section according to claim 8, wherein said second elastic means comprises a locker, splined to said piston, having a plurality of one way holes, a striker which has a plurality of fixing hooks with which mesh said plurality of one way holes of said locker, and which is stricken by a supporting portion of said piston, and which is incorporated to said piston to rotate freely, and a spring which is disposed between said locker and said striker to enable said holes of said locker to be engaged to said hooks.

10. An apparatus for operating a biopsy needle with an elliptical hollow cross section, comprising:

a cylinder having a first port and a second port for receiving compressed air, a third port, and a fourth port, said third and fourth ports communicating with each other;

a rotation blade, which has a central hollow axis, driven by compression air passing from said third port to said fourth port;

a piston, which is splined to said central hollow axis, for a straight movement and rotation movement in said cylinder; and a plate which is fixed to said piston, defines two separated chambers of said cylinder, and moves between said first port and said second port as said piston moves, thereby selectively opens said third port.

\* \* \* \* \*